US011426544B2

(12) United States Patent
Malgat et al.

(10) Patent No.: US 11,426,544 B2
(45) Date of Patent: Aug. 30, 2022

(54) AEROSOL-GENERATING SYSTEM COMPRISING A DELIVERY ENHANCING COMPOUND SOURCE AND A MEDICAMENT SOURCE

(71) Applicant: Philip Morris Products S.A., Neuchatel (CH)

(72) Inventors: Alexandre Malgat, Les Tuileries de Grandson (CH); Judith Waller, Peseux (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 1337 days.

(21) Appl. No.: 14/890,366

(22) PCT Filed: May 19, 2014

(86) PCT No.: PCT/EP2014/060204
§ 371 (c)(1),
(2) Date: Nov. 10, 2015

(87) PCT Pub. No.: WO2014/187763
PCT Pub. Date: Nov. 27, 2014

(65) Prior Publication Data
US 2016/0120220 A1    May 5, 2016

(30) Foreign Application Priority Data
May 21, 2013    (EP) .................................... 13168613

(51) Int. Cl.
*A61M 15/06*        (2006.01)
*A24F 40/30*        (2020.01)
(Continued)

(52) U.S. Cl.
CPC ............. *A61M 15/06* (2013.01); *A24F 40/30* (2020.01); *A24F 40/42* (2020.01); *A61M 11/00* (2013.01);
(Continued)

(58) Field of Classification Search
CPC ...... A24F 47/004; A24F 47/008; A24F 40/10; A24F 40/32; A24F 40/40; A61M 11/00;
(Continued)

(56) References Cited

U.S. PATENT DOCUMENTS 4,830,028 A   5/1989 Lawson et al.
4,836,224 A   6/1989 Lawson et al.
(Continued)

FOREIGN PATENT DOCUMENTS

CN    1039530 A     2/1990
CN    102355914 A   2/2012
(Continued)

OTHER PUBLICATIONS

International Search Report and Written Opinion dated Jun. 12, 2014 for PCT/EP2014/060204 filed on May 19, 2014.
(Continued)

*Primary Examiner* — Colin W Stuart
*Assistant Examiner* — Douglas Y Sul
(74) *Attorney, Agent, or Firm* — Oblon, McClelland, Maier & Neustadt, L.L.P.

(57) ABSTRACT

An aerosol-generating system is provided, including a medicament source and a volatile delivery enhancing compound source. The volatile delivery enhancing compound source includes a first sorption element, a second sorption element downstream of the first sorption element, and a volatile delivery enhancing compound sorbed on the first sorption element and the second sorption element, wherein a rate of release of the volatile delivery enhancing compound from
(Continued)

the first sorption element is greater than a rate of release of the volatile delivery enhancing compound from the second sorption element.

18 Claims, 2 Drawing Sheets

(51) Int. Cl.
  *A24F 40/42* (2020.01)
  *A61M 11/00* (2006.01)
  *A61M 15/00* (2006.01)
  *A24F 40/10* (2020.01)
  *A61M 11/04* (2006.01)

(52) U.S. Cl.
  CPC .............. *A24F 40/10* (2020.01); *A61M 11/04* (2013.01); *A61M 15/0003* (2014.02); *A61M 2205/36* (2013.01)

(58) Field of Classification Search
  CPC ... A61M 11/04; A61M 15/0003; A61M 15/06
  See application file for complete search history.

(56) References Cited

U.S. PATENT DOCUMENTS

| | | | |
|---|---|---|---|
| 4,898,190 | A | 2/1990 | Deal |
| 5,050,621 | A | 9/1991 | Creighton et al. |
| 5,546,965 | A | 8/1996 | White |
| 7,431,570 | B2 * | 10/2008 | Young .................... F04B 17/00 137/833 |
| 2004/0129793 | A1 | 7/2004 | Nguyen et al. |
| 2004/0151598 | A1 | 8/2004 | Young et al. |
| 2008/0241255 | A1 * | 10/2008 | Rose ................. A61K 31/4439 424/489 |
| 2012/0006342 | A1 | 1/2012 | Rose et al. |
| 2012/0255567 | A1 | 10/2012 | Rose et al. |

FOREIGN PATENT DOCUMENTS

| | | |
|---|---|---|
| EP | 0 212 234 A2 | 3/1987 |
| EP | 0 354 661 A2 | 2/1990 |
| EP | 0 539 674 A1 | 5/1993 |
| JP | 0349383 U | 9/1944 |
| JP | 2012-520736 A | 9/2012 |
| TW | 201315395 A1 | 4/2013 |
| WO | WO 2008/015441 A1 | 2/2008 |
| WO | WO 2008/121610 A1 | 10/2008 |
| WO | 2010/107613 A1 | 9/2010 |
| WO | WO 2011/034723 A1 | 3/2011 |
| WO | WO 2011/160788 A1 | 12/2011 |

OTHER PUBLICATIONS

Combined Chinese Office Action and Search Report dated Jun. 5, 2018 in Patent Application No. 201480025198.7 (with English language translation).
Combined Russian Office Action and Search Report dated Mar. 26, 2018 in Patent Application No. 2015154179 (with English language translation and English translation of categories of cited documents), 11 pages.
Office Action dated Mar. 19, 2018 in Japanese Patent Application No. 2016-514352 (with English language translation), 12 pages.
Decision on Gant dated Jun. 29, 2017 in Kazakhstan patent application No. 2015/1445.1 (with English translation).
Combined Office Action and Search Report dated Dec. 13, 2018 in corresponding Taiwanese Patent Application No. 103117444 (with English Translation), 6 pages.
Extended Search Report dated Nov. 7, 2013 in European Patent Application No. 13168613.1.
Office Action dated Aug. 28, 2020 in corresponding Korean Patent Application No. 10-2015-7030745 (with English translation), 10 pages.

\* cited by examiner

AEROSOL-GENERATING SYSTEM COMPRISING A DELIVERY ENHANCING COMPOUND SOURCE AND A MEDICAMENT SOURCE

The present invention relates to an aerosol-generating system and an aerosol-generating article for use in an aerosol-generating system. In particular, the present invention relates to an aerosol-generating system for generating an aerosol comprising nicotine salt particles and an aerosol-generating article for use in such an aerosol-generating system.

WO 2008/121610 A1, WO 2010/107613 A1 and WO 2011/034723 A1 disclose devices for delivering nicotine or other medicaments to a user comprising a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

FIGS. 2A-2C of WO 2010/107613 A1 show an exemplary device having a sequential configuration, which is used in Experiment #8 of WO 2010/107613 A1. As shown in FIGS. 2A-2C and described in paragraph [0052] and Experiment #8 of WO 2010/107613 A1, this experimental device comprises a tobacco source element 20 (moistened tobacco mixture packed in between rolled stainless steel screen and Teflon outer housing) and a pyruvic acid source element 30 (pyruvic acid in air-freshener plug) separated by a gap 60.

It would be desirable to provide an aerosol-generating system of the type disclosed in WO 2008/121610 A1, WO 2010/107613 A1 and WO 2011/034723 A1 in which the delivery of nicotine salt particles to a user is improved. It would be especially desirable to provide an aerosol-generating system of the type disclosed in WO 2008/121610 A1, WO 2010/107613 A1 and WO 2011/034723 A1 in which the consistency of nicotine salt particle delivery to a user is improved.

It would also be desirable to provide an aerosol-generating system of the type disclosed in WO 2008/121610 A1, WO 2010/107613 A1 and WO 2011/034723 A1 that allows for improved control of the delivery of nicotine salt particles to a user.

According to the invention there is provided an aerosol-generating system comprising: a medicament source; and a volatile delivery enhancing compound source, the volatile delivery enhancing compound source comprising: a first sorption element; a second sorption element downstream of the first sorption element; and a volatile delivery enhancing compound sorbed on the first sorption element and the second sorption element, wherein the rate of release of the volatile delivery enhancing compound from the first sorption element is greater than the rate of release of the volatile delivery enhancing compound from the second sorption element.

According to the invention there is also provided an aerosol-generating system comprising: an aerosol-generating article, the aerosol-generating article comprising: a medicament source; and a volatile delivery enhancing compound source, the volatile delivery enhancing compound source comprising: a first sorption element; a second sorption element downstream of the first sorption element; and a volatile delivery enhancing compound sorbed on the first sorption element and the second sorption element, wherein the rate of release of the volatile delivery enhancing compound from the first sorption element is greater than the rate of release of the volatile delivery enhancing compound from the second sorption element.

According to the invention there is further provided an aerosol-generating system comprising: an aerosol-generating article comprising: a medicament source; and a volatile delivery enhancing compound source, the volatile delivery enhancing compound source comprising: a first sorption element; a second sorption element downstream of the first sorption element; and a volatile delivery enhancing compound sorbed on the first sorption element and the second sorption element, wherein the rate of release of the volatile delivery enhancing compound from the first sorption element is greater than the rate of release of the volatile delivery enhancing compound from the second sorption element; and an aerosol-generating device in cooperation with the aerosol-generating article, the aerosol generating device comprising heating means for heating one or both of the medicament source and the volatile delivery enhancing compound source of the aerosol-generating article.

According to the invention there is further provided an aerosol-generating article for use in an aerosol-generating system according to the invention, the aerosol-generating article comprising: a medicament source; and a volatile delivery enhancing compound source, the volatile delivery enhancing compound source comprising: a first sorption element; a second sorption element downstream of the first sorption element; and a volatile delivery enhancing compound sorbed on the first sorption element and the second sorption element, wherein the rate of release of the volatile delivery enhancing compound from the first sorption element is greater than the rate of release of the volatile delivery enhancing compound from the second sorption element.

As used herein, the term "volatile" refers to a delivery enhancing compound having a vapour pressure of at least about 20 Pa. Unless otherwise stated, all vapour pressures referred to herein are vapour pressures at 25° C. measured in accordance with ASTM E1194-07.

As used herein, by "sorbed" it is meant that the delivery enhancing compound is adsorbed on the surface of the sorption element, or absorbed in the sorption element, or both adsorbed on and absorbed in the sorption element.

As used herein, the term "aerosol-generating device" refers to a device that interacts with an aerosol-generating article to generate an aerosol that is directly inhalable into a user's lungs thorough the user's mouth.

As used herein, the terms "upstream", "downstream", "proximal" and "distal" are used to describe the relative positions of components, or portions of components, of aerosol-generating articles and aerosol-generating systems according to the invention.

The aerosol-generating article or system comprises a proximal end through which, in use, an aerosol exits the aerosol-generating article or system. The proximal end may also be referred to as the mouth end. In use, a user draws on the proximal or mouth end of the aerosol-generating article or system in order to inhale an aerosol generated by the aerosol-generating article or system. The aerosol-generating article or system comprises a distal end opposed to the proximal or mouth end. The proximal or mouth end of the aerosol-generating article or system may also be referred to as the downstream end and the distal end of the aerosol-generating article or system may also be referred to as the upstream end. Components, or portions of components, of the aerosol-generating article or system may be described as being upstream or downstream of one another based on their relative positions between the proximal or downstream end and the distal or upstream end of the aerosol-generating article or system.

The upstream and downstream ends of the aerosol-generating article are defined with respect to the airflow when a user draws on the proximal or mouth end of the aerosol-generating article. Air is drawn into the aerosol-generating article at the distal or upstream end, passes downstream through the aerosol-generating article and exits the aerosol-generating article at the proximal or downstream end.

As used herein, the term "longitudinal" is used to describe the direction between the downstream or proximal end and the opposed upstream or distal end and the term "transverse" is used to describe the direction perpendicular to the longitudinal direction.

The rate of release of the delivery enhancing compound from the first sorption element of the delivery enhancing compound source of aerosol-generating systems according to the invention at a given temperature is greater than the rate of release of the delivery enhancing compound from the second sorption element of the delivery enhancing compound source of aerosol-generating systems according to the invention. As described further below, in use the inclusion of a delivery enhancing compound source comprising a first sorption element and a second sorption element that release the delivery enhancing compound at different rates advantageously improves the delivery of the medicament to a user. In particular, the inclusion of a delivery enhancing compound source comprising a first sorption element and a second sorption element that release the delivery enhancing compound at different rates advantageously improves the consistency of the medicament delivery to a user.

The inclusion in aerosol-generating systems according to the invention of a delivery enhancing compound source comprising a first sorption element and a second sorption element that release the delivery enhancing compound at different rates also advantageously allows for improved control of the delivery of the medicament to a user.

Preferably, the rate of release of the delivery enhancing compound from the first sorption element is at least two times the rate of release of the delivery enhancing compound from the second sorption element. More preferably, the rate of release of the delivery enhancing compound from the first sorption element is at least three times the rate of release of the delivery enhancing compound from the second sorption element.

In certain embodiments, the rate of release of the delivery enhancing compound from the first sorption element may be between about two times and about ten times the rate of release of the delivery enhancing compound from the second sorption element. In other embodiments, the rate of release the rate of release of the delivery enhancing compound from the first sorption element may be between about three times and about ten times the rate of release of the delivery enhancing compound from the second sorption element.

The air permeability of the first sorption element may be greater than the air permeability of the second sorption element. In such embodiments the increased air permeability of the first sorption element relative to the second sorption element may increase the rate of release of the delivery enhancing compound from the first sorption element relative to the rate of release of the delivery enhancing compound from the second sorption element.

Preferably, the air permeability of the first sorption element as measured in accordance with ISO 2965:2009 is at least 1.5 times the air permeability of the second sorption element. More preferably, the air permeability of the first sorption element as measured in accordance with ISO 2965:2009 is at least 2 times the air permeability of the second sorption element.

In certain embodiments, the air permeability of the first sorption element as measured in accordance with ISO 2965:2009 may be between about 1.5 times and about 10 times the air permeability of the second sorption element, preferably between about 1.5 times and about 5 times the air permeability of the second sorption element. In other embodiments, the air permeability of the first sorption element as measured in accordance with ISO 2965:2009 may be between about 2 times and about 10 times the air permeability of the second sorption element, preferably between about 2 times and about 5 times the air permeability of the second sorption element.

In certain preferred embodiments the first sorption element may have an air permeability of between about 250 Coresta units and about 300 Coresta units as measured in accordance with ISO 2965:2009 and the second sorption element may have an air permeability of between about 100 Coresta units and about 150 Coresta units as measured in accordance with ISO 2965:2009.

The air permeability in Coresta units is the amount of air in cubic centimetres that passes through one square centimetre of the sorption element in one minute at a constant pressure difference of one kilopascal (that is, 1 Coresta unit corresponds to an air permeability of 1 $cm^3/min \cdot cm^2$ at a pressure differential of 1 kPa).

Alternatively or in addition, the porosity of the first sorption element may be greater than the porosity of the second sorption element. In such embodiments the increased porosity of the first sorption element relative to the second sorption element may increase the rate of release of the delivery enhancing compound from the first sorption element relative to the rate of release of the delivery enhancing compound from the second sorption element.

Preferably, the porosity of the first sorption element as measured by mercury porosimetry in accordance with ISO 15901-1:2005 is at least 1.5 times the porosity of the second sorption element. More preferably, the porosity of the first sorption element as measured by mercury porosimetry is at least two times the porosity of the second sorption element.

In certain preferred embodiments the first sorption element may have a porosity of between about 20% and about 50% as measured by mercury porosimetry in accordance with ISO 15901-1:2005 and the second sorption element may have a porosity of between about 5% and about 35% as measured by mercury porosimetry in accordance with ISO 15901-1:2005.

In certain embodiments, the porosity of the first sorption element as measured by mercury porosimetry in accordance with ISO 15901-1:2005 may be between about 1.5 times and about 10 times the porosity of the second sorption element, preferably between about 1.5 times and about 5 times the porosity of the second sorption element. In other embodiments, the porosity of the first sorption element as measured by mercury porosimetry in accordance with ISO 15901-1:2005 may be between about 2 times and about 10 times the porosity of the second sorption element, preferably between about 2 times and about 5 times the porosity of the second sorption element.

Alternatively or in addition, the polarity of the second sorption element may be greater than the polarity of the second sorption element. This is particularly preferred where the volatile delivery enhancing compound is a polar compound. In such embodiments the increased polarity of the second sorption element relative to the first sorption element may decrease the rate of release of the delivery enhancing compound from the second sorption element relative to the rate of release of the delivery enhancing compound from the first sorption element.

The second sorption element may be immediately downstream of and in contact with the first sorption element.

Alternatively, the second sorption element may be spaced apart from the first sorption element.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

In certain embodiments, the volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

In other embodiments, the volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

In further embodiments, the volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

In yet further embodiments, the volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound.

Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

In one embodiment, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid.

In a preferred embodiment, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. In a particularly preferred embodiment, the volatile delivery enhancing compound comprises pyruvic acid.

Preferably, the delivery enhancing compound is adsorbed on the first sorption element and the second sorption element.

The first sorption element and the second sorption element act as reservoirs for the volatile delivery enhancing compound.

The first sorption element and the second sorption element may be formed from the same or different materials.

The first sorption element and the second sorption element may be formed from any suitable material or combination of materials. For example, the first sorption element and the second sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, at least one of the first sorption element and the second sorption element is a porous sorption element.

For example, at least one of the first sorption element and the second sorption element may be a porous sorption element comprising one or more materials selected from the group consisting of porous plastic materials, porous polymer fibres and porous glass fibres.

In a particularly preferred embodiment, both the first sorption element and the second sorption element are porous sorption elements.

The first sorption element and the second sorption element are preferably chemically inert with respect to the volatile delivery enhancing compound.

The first sorption element and the second sorption element may have any suitable shape and dimensions.

The first sorption element and the second sorption element may have the same or different shape and dimensions. Preferably, the first sorption element and the second sorption element are of the substantially the shape and dimensions.

In one embodiment, at least one of the first sorption element and the second sorption element is a cylindrical plug. In one preferred embodiment, at least one of the first sorption element and the second sorption element is a porous substantially cylindrical plug. In one particularly preferred embodiment, both the first sorption element and the second sorption element are porous substantially cylindrical plugs.

In another embodiment, at least one of the first sorption element and the second sorption element is a substantially cylindrical hollow tube. In another preferred embodiment, at least one of the first sorption element and the second sorption element is a porous substantially cylindrical hollow tube.

The size, shape and composition of the first sorption element and the second sorption element may be chosen to allow a desired amount of the volatile delivery enhancing compound to be sorbed on the first sorption element and the second sorption element.

Preferably, the volatile delivery enhancing compound source comprises a total of between about 200 μl and about 600 μl, more preferably between about 250 μl and about 550 μl, most preferably between about 300 μl and about 500 μl of the volatile delivery enhancing compound.

The first sorption element and the second sorption element act as reservoirs for the volatile delivery enhancing compound.

Preferably, the amount of the volatile delivery enhancing compound adsorbed on the first sorption element is greater than the amount of the volatile delivery enhancing compound adsorbed on the second sorption element. In such embodiments the first sorption element advantageously acts as a main reservoir of the volatile delivery enhancing compound and the second sorption element acts as a minor reservoir of the volatile delivery enhancing compound.

Preferably, at least about 150 μl, more preferably at least about 200 μl, most preferably at least about 250 μl of the volatile delivery enhancing compound is sorbed on the first sorption element.

For example, between about 150 μl and about 450 μl, more preferably between about 200 μl and about 400 μl, most preferably between about 225 μl and about 375 μl of the volatile delivery enhancing compound may be sorbed on the first sorption element.

Preferably, at least about 20 μl, more preferably at least about 50 μl, most preferably at least about 75 μl of the volatile delivery enhancing compound is sorbed on the second sorption element.

For example, between about 20 μl and about 200 μl, more preferably between about 50 μl and about 150 μl, most preferably between about 75 μl and about 125 μl of the volatile delivery enhancing compound may be sorbed on the second sorption element.

The medicament source preferably comprises a medicament having a melting point below about 150 degrees Celsius. Alternatively or in addition, preferably the medicament has a boiling point below about 300 degrees Celsius.

In certain preferred embodiments, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(I-methyl-2-pyrrolidinyl)isoxazole (ABT 418) and (±)-2-(3-Pyridinyl)-I-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

In preferred embodiments, the medicament source is a nicotine source.

The nicotine source may comprise one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

The medicament source may comprise a third sorption element and a medicament sorbed on the third sorption element. In preferred embodiments where the medicament source is a nicotine source, the nicotine source may comprise a third sorption element and nicotine sorbed on the third sorption element.

The third sorption element acts as a reservoir for the nicotine or other medicament.

The third sorption element may be formed from the same or different materials to the first sorption element and the second sorption element.

The third sorption element may be formed from any suitable material or combination of materials. For example, the third sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the third sorption element is a porous sorption element.

For example, the third sorption element may be a porous sorption element comprising one or more materials selected from the group consisting of porous plastic materials, porous polymer fibres and porous glass fibres.

The third sorption element is preferably chemically inert with respect to the nicotine or other medicament.

The third sorption element may have any suitable shape and dimensions.

The third sorption element may have the same or different shape and dimensions to the first sorption element and the second sorption element.

In one embodiment, the third sorption element is a cylindrical plug. In one preferred embodiment, the third sorption element is a porous substantially cylindrical plug.

In another embodiment, the third sorption element is a substantially cylindrical hollow tube. In another preferred embodiment, the third sorption element is a porous substantially cylindrical hollow tube.

The size, shape and composition of the third sorption element may be chosen to allow a desired amount of the nicotine or other medicament to be sorbed on the third sorption element.

Preferably, the medicament source comprises between about 10 µl and about 300 µl, more preferably between about 20 µl and about 200 µl, most preferably between about 50 µl and about 250 µl of the nicotine or other medicament.

In a preferred embodiment the aerosol-generating system comprises: an aerosol-generating article comprising the medicament source and the volatile delivery enhancing compound source.

Preferably, the aerosol-generating article comprises: a first compartment comprising a first one of the medicament source and the volatile delivery enhancing compound source; and a second compartment comprising a second one of the medicament source and the volatile delivery enhancing compound source.

Preferably, the first compartment comprises the volatile delivery enhancing compound source and the second compartment comprises the medicament source. However, it will be appreciated that the first compartment may alternatively comprise the medicament source and the second compartment may alternatively comprise the volatile delivery enhancing compound source.

The first compartment and the second compartment of the aerosol-generating article may abut one another. Alternatively, the first compartment and the second compartment of the aerosol-generating article may be spaced apart from one another.

The first compartment of the aerosol-generating article may be sealed by one or more frangible barriers. In a preferred embodiment, the first compartment is sealed by a pair of opposed transverse frangible barriers.

Alternatively or in addition, the second compartment of the aerosol-generating article may be sealed by one or more frangible barriers. In a preferred embodiment, the second compartment is sealed by a pair of opposed transverse frangible barriers.

The one or more frangible barriers may be formed from any suitable material. For example, the one or more frangible barriers may be formed from a metal foil or film.

The volume of the first compartment and the second compartment may be the same or different. In a preferred embodiment, the volume of the second compartment is greater than the volume of the first compartment.

As described further below, the first compartment and the second compartment may be arranged in series or parallel within the aerosol-generating article.

As used herein, by "series" it is meant that the first compartment and the second compartment are arranged within the aerosol-generating article so that in use an air stream drawn through the aerosol-generating article passes through one of the first compartment and the second compartment and then passes through the other of the first compartment and the second compartment.

In embodiments in which the first compartment comprises the volatile delivery enhancing compound source and the second compartment comprises the medicament source, volatile delivery enhancing compound vapour is released from the volatile delivery enhancing compound source in the first compartment into the air stream drawn through the aerosol-generating article and medicament vapour is released from the medicament source in the second compartment into the air stream drawn through the aerosol-generating article. The volatile delivery enhancing compound vapour reacts with the medicament vapour in the gas phase to form an aerosol, which is delivered to a user.

In embodiments in which the first compartment comprises the medicament source and the second compartment comprises the volatile delivery enhancing compound source, medicament vapour is released from the medicament source in the first compartment into the air stream drawn through the aerosol-generating article and volatile delivery enhancing compound vapour is released from the volatile delivery enhancing compound source in the second compartment into the air stream drawn through the aerosol-generating article. The medicament vapour reacts with the volatile delivery enhancing compound vapour in the gas phase to form an aerosol, which is delivered to a user.

Where the first compartment and the second compartment are arranged in series within the aerosol-generating article, the second compartment is preferably downstream of the first compartment so that in use an air stream drawn through the aerosol-generating article passes through the first compartment and then passes through the second compartment. However, it will be appreciated that the second compartment may alternatively be upstream of the first compartment so that in use an air stream drawn through the aerosol-generating article passes through the second compartment and then passes through the first compartment.

In embodiments where the second compartment is downstream of the first compartment, the volatile delivery enhancing compound vapour may react with the medicament vapour in the second compartment. In such embodiments the aerosol-generating article may further comprise a third compartment downstream of the second compartment and the volatile delivery enhancing compound vapour may alternatively or in addition react with the medicament vapour in the third compartment to form an aerosol.

In embodiments where the second compartment is upstream of the first compartment, the volatile delivery enhancing compound vapour may react with the medicament vapour in the first compartment. In such embodiments the aerosol-generating article may further comprise a third compartment downstream of the first compartment and the volatile delivery enhancing compound vapour may alternatively or in addition react with the medicament vapour in the third compartment to form an aerosol.

As used herein, by "parallel" it is meant that the first compartment and the second compartment are arranged within the aerosol-generating article so that in use a first air stream drawn through the aerosol-generating article passes through the first compartment and a second air stream drawn through the aerosol-generating article passes through the second compartment.

In embodiments in which the first compartment comprises the volatile delivery enhancing compound source and the second compartment comprises the medicament source, volatile delivery enhancing compound vapour is released from the volatile delivery enhancing compound source in the first compartment into the first air stream drawn through the aerosol-generating article and medicament vapour is released from the medicament source in the second compartment into the second air stream drawn through the aerosol-generating article. The volatile delivery enhancing compound vapour in the first air stream reacts with the medicament vapour in the second air stream in the gas phase to form an aerosol, which is delivered to a user.

In such embodiments the aerosol-generating article may further comprise a third compartment downstream of the first compartment and the second compartment and the volatile delivery enhancing compound vapour in the first air stream may mix and react with the medicament vapour in the second air stream in the third compartment to form an aerosol.

In embodiments in which the first compartment comprises the medicament source and the second compartment comprises the volatile delivery enhancing compound source, medicament vapour is released from the medicament source in the first compartment into the first air stream drawn through the aerosol-generating article and volatile delivery enhancing compound vapour is released from the volatile delivery enhancing compound source in the second compartment into the second air stream drawn through the aerosol-generating article. The medicament vapour in the first air stream reacts with the volatile delivery enhancing compound vapour in the second air stream in the gas phase to form an aerosol, which is delivered to a user.

In such embodiments the aerosol-generating article may further comprise a third compartment downstream of the first compartment and the second compartment and the medicament vapour in the first air stream may mix and react with the volatile delivery enhancing compound vapour in the second air stream in the third compartment to form an aerosol.

In particularly preferred embodiments, the aerosol-generating article comprises: a housing comprising: an air inlet; a first compartment in communication with the air inlet, the first compartment comprising a first one of the medicament source and the volatile delivery enhancing compound source; a second compartment in communication with the first compartment, the second compartment comprising a second one of the medicament source and the volatile delivery enhancing compound source; and an air outlet, wherein the air inlet and the air outlet are in communication with each other and configured so that air may pass into the housing through the air inlet, through the housing and out of the housing through the air outlet.

As used herein, the term "air inlet" is used to describe one or more apertures through which air may be drawn into the aerosol-generating article.

As used herein, the term "air outlet" is used to describe one or more apertures through which air may be drawn out of the aerosol-generating article.

In such embodiments, the first compartment and the second compartment are arranged in series from air inlet to air outlet within the housing. That is, the first compartment is downstream of the air inlet, the second compartment is downstream of the first compartment and the air outlet is downstream of the second compartment. In use, a stream of air is drawn into the housing through the air inlet, downstream through the first compartment and the second compartment and out of the housing through the air outlet.

The aerosol-generating article may further comprise a third compartment in communication with: the second compartment; and the air outlet. In use in such embodiments, a stream of air is drawn into the housing through the air inlet, downstream through the first compartment, the second compartment and the third compartment and out of the housing through the air outlet.

The aerosol-generating article may further comprise a mouthpiece in communication with: the second compartment or the third compartment, where present; and the air outlet. In use in such embodiments, a stream of air is drawn into the housing through the air inlet, downstream through the first compartment, the second compartment, the third compartment, where present, and the mouthpiece and out of the housing through the air outlet.

In other preferred embodiments, the aerosol-generating article comprises: a housing comprising: an air inlet; a first compartment in communication with the air inlet, the first compartment comprising a first one of the medicament source and the volatile delivery enhancing compound source; a second compartment in communication with the air inlet, the second compartment comprising a second one of the medicament source and the volatile delivery enhancing compound source; and an air outlet, wherein the air inlet and the air outlet are in communication with each other and configured so that air may pass into the housing through the air inlet, through the housing and out of the housing through the air outlet.

In such embodiments, the first compartment and the second compartment are arranged in parallel from air inlet to air outlet within the housing. The first compartment and the second compartment are both downstream of the air inlet and upstream of the air outlet. In use, a stream of air is drawn into the housing through the air inlet, a first portion of the stream of air is drawn downstream through the first compartment and a second portion of the stream of air is drawn downstream through the second compartment.

The aerosol-generating article may further comprise a third compartment in communication with: one or both of the first compartment and the second compartment; and the air outlet.

The aerosol-generating article may further comprise a mouthpiece in communication with: the first compartment and the second compartment, or the third compartment, where present; and the air outlet.

In further preferred embodiments, the aerosol-generating article comprises: a housing comprising: a first air inlet; a second air inlet; a first compartment in communication with the first air inlet, the first compartment comprising a first one of the medicament source and the volatile delivery enhancing compound source; a second compartment in communication with the second air inlet, the second compartment comprising a second one of the medicament source and the volatile delivery enhancing compound source; and an air outlet, wherein the first air inlet, the second air inlet and the air outlet are in communication with each other and configured so that air may pass into the housing through the first air inlet, through the housing and out of the housing through the air outlet and air may pass into the housing through the second air inlet, through the housing and out of the housing through the air outlet.

In such embodiments, the first compartment and the second compartment are arranged in parallel within the housing. The first compartment is downstream of the first air inlet and upstream of the air outlet and the second compartment is downstream of the second air inlet and upstream of the air outlet. In use, a first stream of air is drawn into the housing through the first air inlet and downstream through the first compartment and a second stream of air is drawn into the housing through the second air inlet and downstream through the second compartment.

The aerosol-generating article may further comprise a third compartment in communication with: one or both of the first compartment and the second compartment; and the air outlet.

The aerosol-generating article may further comprise a mouthpiece in communication with: the first compartment and the second compartment, or the third compartment, where present; and the air outlet.

The housing of the aerosol-generating article may simulate the shape and dimensions of a tobacco smoking article, such as a cigarette, a cigar, a cigarillo or a pipe, or a cigarette pack. In a preferred embodiment, the housing simulates the shape and dimensions of a cigarette.

Where present, the third compartment may comprise one or more aerosol-modifying agents. For example, the third compartment may comprise an adsorbent, such as activated carbon, a flavourant, such as menthol, or a combination thereof.

Where present, the mouthpiece may comprise a filter. The filter may have a low particulate filtration efficiency or very low particulate filtration efficiency. Alternatively, the mouthpiece may comprise a hollow tube.

In a preferred embodiment the aerosol-generating system comprises: an aerosol-generating article comprising the medicament source and the volatile delivery enhancing compound source; and an aerosol-generating device in cooperation with the aerosol-generating article, the aerosol generating device comprising heating means for heating one or both of the medicament source and the volatile delivery enhancing compound source of the aerosol-generating article.

The aerosol-generating device preferably comprises a cavity configured to receive at least a portion of the aerosol-generating article.

In embodiments where the aerosol-generating article comprises: a first compartment comprising a first one of the medicament source and the volatile delivery enhancing compound source; and a second compartment comprising a second one of the medicament source and the volatile delivery enhancing compound source, the aerosol-generating device preferably comprises a cavity configured to receive the first compartment and the second compartment of the aerosol-generating article.

Preferably, the cavity of the aerosol-generating device is substantially cylindrical.

The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

As used herein, the term "transverse cross-section" is used to describe the cross-section of the cavity perpendicular to the major axis of the cavity.

Preferably, the cavity of the aerosol-generating device has a transverse cross-section of substantially the same shape as the transverse cross-section of the aerosol-generating article.

In certain embodiments, the cavity of the aerosol-generating device may have a transverse cross-section of substantially the same shape and dimensions as the transverse cross-section of the aerosol-generating article to be received in the cavity in order to maximize conductive thermal transfer from the aerosol-generating device to the aerosol-generating article.

Preferably, the cavity of the aerosol-generating device is of substantially circular transverse cross-section or of substantially elliptical transverse cross-section. Most preferably, the cavity of the aerosol-generating device is of substantially circular transverse cross-section.

Preferably, the length of the cavity of the aerosol-generating device is less than the length of the aerosol-generating article so that when the aerosol-generating article is received in the cavity of the aerosol-generating device the proximal or downstream end of the aerosol-generating article projects from the cavity of the aerosol-generating device.

As used herein, by "length" is meant the maximum longitudinal dimension between the distal or upstream end and the proximal or downstream end of the cavity and aerosol-generating article.

Preferably, the cavity of the aerosol-generating device has a diameter substantially equal to or slightly greater than the diameter of the aerosol-generating article.

As used herein, by "diameter" is meant the maximum transverse dimension of the cavity and aerosol-generating article.

In embodiments where one or both of the first compartment and the second compartment of the aerosol-generating article is sealed by one or more frangible seals, the aerosol-generating device may further comprise a piercing member positioned within the cavity for piercing the first and second compartments of the aerosol-generating article. The piercing member may be formed from any suitable material.

Where the first compartment and the second compartment of the aerosol-generating article are arranged in series within the aerosol-generating article, the piercing member is preferably positioned centrally within the cavity of the aerosol-generating device, along the major axis of the cavity.

Where the first compartment and the second compartment of the aerosol-generating article are arranged in parallel within the aerosol-generating article, the piercing member may comprise a first piercing element positioned within the cavity of the aerosol-generating device for piercing the first compartment of the aerosol-generating article and a second piercing element positioned within the cavity of the aerosol-generating device for piercing the second compartment of the aerosol-generating article.

The aerosol generating device comprises heating means for heating one or both of the medicament source and the volatile delivery enhancing compound source of the aerosol-generating article.

The heating means may be a non-electrical heating means.

In certain embodiments the heating means may comprise a heat sink or heat exchanger configured to transfer thermal energy from an external heat source to one or both of the medicament source and the volatile delivery enhancing compound source of the aerosol-generating article. The heat sink or heat exchanger may be formed of any suitable thermally conductive material. Suitable materials include, but are not limited to, metals, such as aluminium and copper.

In certain embodiments, the heating means may comprise a heat sink or heat exchanger configured to transfer thermal energy from a blue flame or torch lighter or other lighter to one or both of the medicament source and the volatile delivery enhancing compound source of the aerosol-generating article. In such embodiments, a user may advantageously use a lighter to activate the aerosol-generating system in a manner similar to lighting a cigarette or other conventional smoking article.

The heat sink or heat exchanger may extend fully or partially along the length of the cavity of the aerosol-generating device.

Alternatively, the heating means may be an electrical heating means powered by an electric power supply.

Where the heating means is an electric heating means, the aerosol-generating device may further comprise an electric power supply and a controller comprising electronic circuitry configured to control the supply of electric power from the electric power supply to the electric heating means. Any suitable electronic circuitry may be used in order to control the supply of power to the electric heating means. The electronic circuitry may be programmable.

Alternatively, the electrical heating means may be powered by an external electric power supply.

The electric power supply may be a DC voltage source. In preferred embodiments, the electric power supply is a battery. For example, the electric power supply may be a Nickel-metal hydride battery, a Nickel cadmium battery, or a Lithium based battery, for example a Lithium-Cobalt, a Lithium-Iron-Phosphate or a Lithium-Polymer battery. The electric power supply may alternatively be another form of electric charge storage device such as a capacitor. The electric power supply may require recharging and may have a capacity that allows for the storage of enough electrical energy for use of the aerosol-generating device with one or more aerosol-generating articles.

The aerosol-generating device may comprise a heating means comprising one or more heating elements. The one or more heating elements may extend fully or partially along the length of the cavity of the aerosol-generating device. The one or more heating elements may extend fully or partially around the circumference of the cavity of the aerosol-generating device.

The aerosol-generating device may further comprise a controller configured to independently control a supply of power to the one or more heating elements.

In one preferred embodiment the heating means comprises one or more heating elements that are heated electrically. However, other heating schemes may be used to heat the one or more heating elements. For example, the one or more heating elements may be heated by conduction from another heat source. Alternatively, the one or more heating elements may be infra-red heating elements or inductive heating elements.

In a particularly preferred embodiment, the heating means comprises one or more heating elements comprising an electrically resistive material. Each heating element may comprise a non-elastic material, for example a ceramic sintered material, such as alumina ($Al_2O_3$) and silicon nitride ($Si_3N_4$), or printed circuit board or silicon rubber. Alternatively, each heating element may comprise an elastic, metallic material, for example an iron alloy or a nickel-chromium alloy. The one or more heating elements may be flexible heating foils on a dielectric substrate, such as polyimide. Alternatively, the one or more heating elements may be metallic grid or grids, flexible printed circuit boards, or flexible carbon fibre heaters.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The aerosol-generating device may further comprise a temperature sensor configured to sense the temperature of the aerosol-generating device.

In such embodiments, the aerosol-generating device may comprise a controller configured to control a supply of power to the one or more heating elements based on the temperature of the aerosol-generating article sensed by the temperature sensor.

The heating means may comprise one or more heating elements formed using a metal having a defined relationship between temperature and resistivity. In such embodiments, the metal may be formed as a track between two layers of suitable insulating materials. Heating elements formed in this manner may be used to both heat and monitor the temperature of the aerosol-generating article.

The aerosol-generating device may further comprise a housing containing the cavity, heating means and, where present, controller, and power source.

Preferably, the housing of the aerosol-generating device is substantially cylindrical.

The housing of the aerosol-generating device may be designed to be grasped or held by a user.

In a preferred embodiment, the aerosol-generating device is a cylindrical heating sleeve.

For the avoidance of doubt, features described above in relation to one aspect of the invention may also be applicable to other aspects of the invention. In particular, features described above in relation to aerosol-generating systems according to the invention may also relate, where appropriate, to aerosol-generating articles according to the invention and vice versa.

The invention will now be further described with reference to the accompanying drawings in which.

Figure 3:
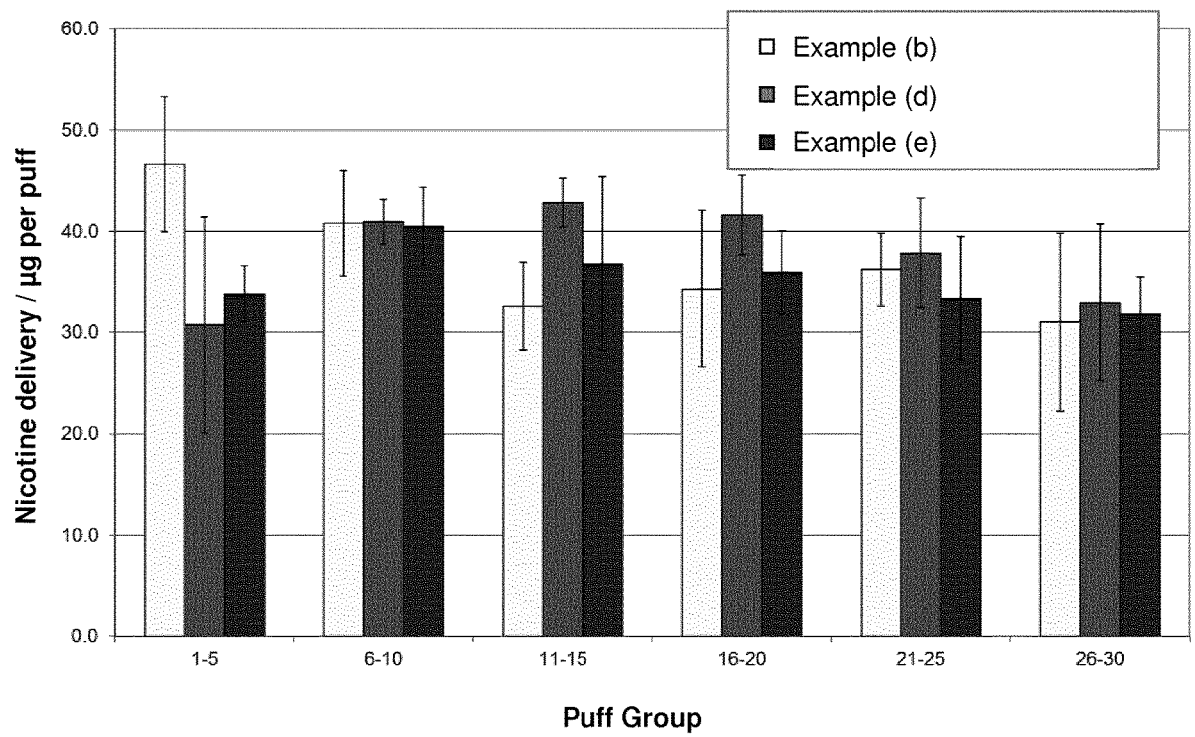
Figure 4:
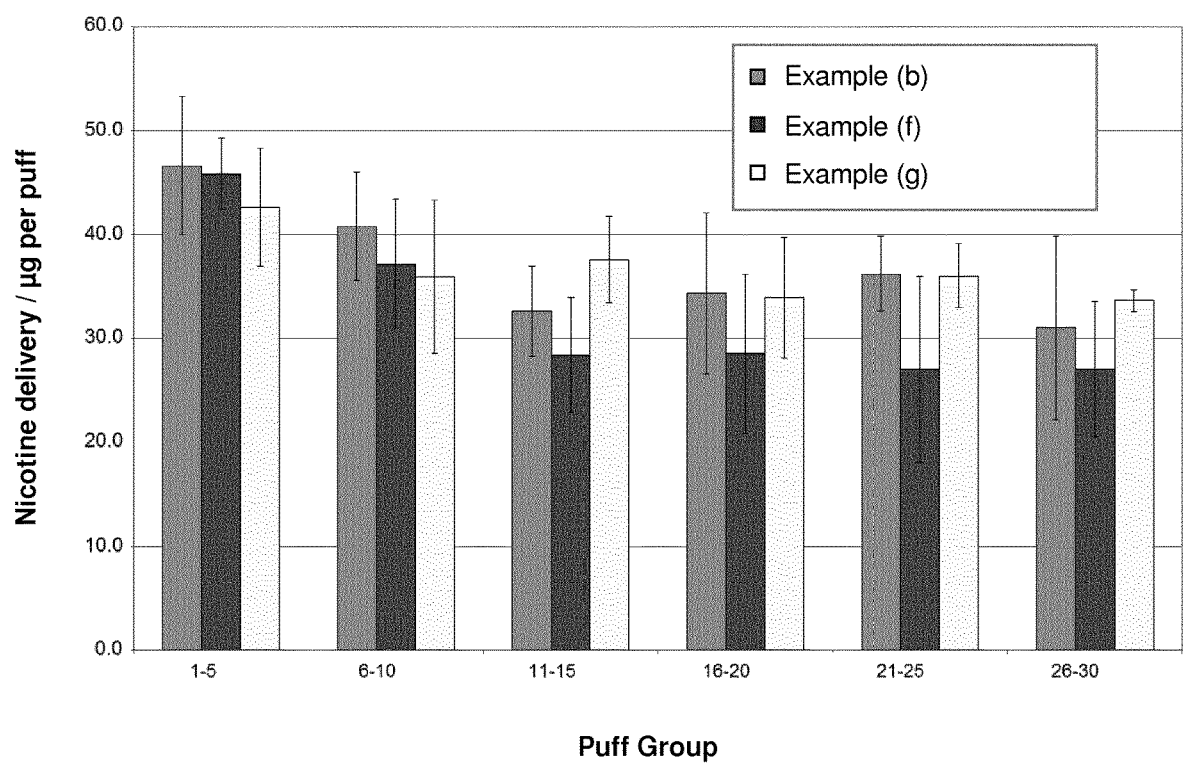

FIG. 3 shows the nicotine delivery per puff as a function of puff number for aerosol-generating articles according to: example (b); example (d); and example (e) upon heating measured under a Health Canada smoking regime; and FIG. 4 shows the nicotine delivery per puff as a function of puff number for aerosol-generating articles according to: example (b); example (f); and example (g) upon heating measured under a Health Canada smoking regime.

Figure 1A:
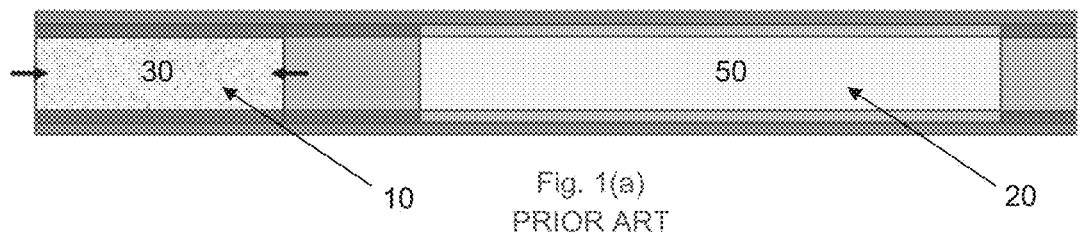
FIG. 1(a) shows a schematic longitudinal cross-section of an aerosol-generating article comprising a medicament source and a volatile delivery enhancing compound source of the type disclosed in WO 2008/121610 A1 and WO 2010/107613 A1.

The prior art aerosol-generating article shown in FIG. 1(a) comprises a pyruvic acid source (10) and a nicotine source (20). As shown in FIG. 1(a), the pyruvic acid source (10) and the nicotine source (20) are arranged in series with the nicotine source (20) downstream of and spaced apart from the pyruvic acid source (10). The pyruvic acid source (10) comprises a porous sorption element (30) with pyruvic acid sorbed thereon and the nicotine source (20) comprises a porous sorption element (50) with nicotine sorbed thereon.

Figure 1B:
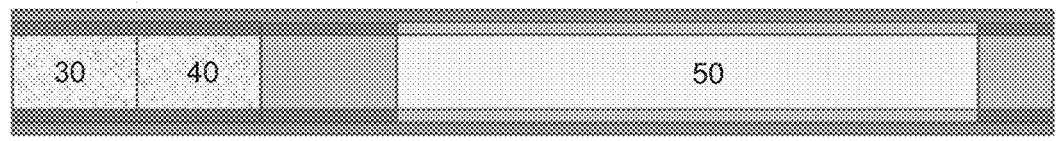
FIG. 1(b) shows a schematic longitudinal cross-section of an aerosol-generating article comprising a medicament source and a volatile delivery enhancing compound source according to a first embodiment of the invention.

The aerosol-generating article according to the first embodiment shown in FIG. 1(b) also comprises a pyruvic acid source (10) and a nicotine source (20) arranged in series with the nicotine source (20) downstream of and spaced apart from the pyruvic acid source (10). However, the aerosol-generating article according to the first embodiment of the invention shown in FIG. 1(b) differs from the prior art aerosol-generating article shown in FIG. 1(a) in that the pyruvic acid source (10) comprises a first porous sorption element (30) with pyruvic acid sorbed thereon and a second porous sorption element (40) with pyruvic acid sorbed thereon. As shown in FIG. 1(b), the first porous sorption element (30) and the second porous sorption element (40) arranged in series with the second porous sorption element (40) immediately downstream of and abutting the first porous sorption element (30).

Figure 1C:
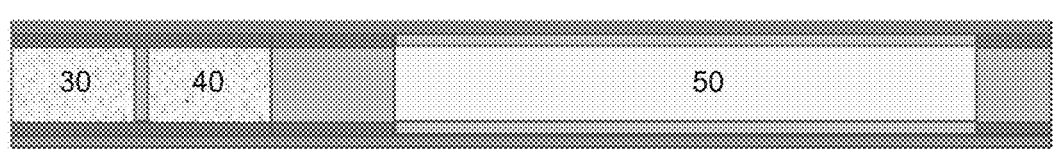
FIG. 1(c) shows a schematic longitudinal cross-section of an aerosol-generating article comprising a medicament source and a volatile delivery enhancing compound source according to a second embodiment of the invention.

The aerosol-generating article according to the second embodiment of the invention shown in FIG. 1(c) is of similar construction to the aerosol-generating article according to the first embodiment shown in FIG. 1(b). However, in the aerosol-generating article according to the second embodiment shown in FIG. 1(c) the second porous sorption element (40) of the pyruvic acid source (10) is downstream of and spaced apart from the first porous sorption element (30) of the pyruvic acid source (10).

COMPARATIVE EXAMPLE (a)

To form a pyruvic acid source 500 µl of pyruvic acid is sorbed by capillarity onto a sintered porous plastic plug with a length of 20 mm and a density of 0.33 g/cm³ having a polyethylene terephthalate (PET) core and a polyethylene (PE) sheath. A suitable porous plastic plug is Porex® XMF-0507 (available from Porex GmbH, Germany).

To form a nicotine source 10 µl of nicotine is sorbed by capillarity onto a sintered porous plastic plug with a length of 50 mm and a density of 0.33 g/cm³ having a polyethylene terephthalate (PET) core and a polyethylene (PE) sheath. A suitable porous plastic plug is Porex® XMF-0507 (available from Porex GmbH, Germany).

A prior art aerosol-generating article having the construction shown in FIG. 1(a) is assembled comprising the pyruvic acid source and the nicotine source. The nicotine source is positioned 10 mm downstream of the pyruvic acid source.

EXAMPLE (b)

To form a pyruvic acid source 250 µl of pyruvic acid is sorbed by capillarity onto a first sintered porous plastic plug with a length of 10 mm and a density of 0.33 g/cm³ having a polyethylene terephthalate (PET) core and a polyethylene (PE) sheath and 100 µl of pyruvic acid is sorbed by capillarity onto a second sintered porous plastic plug with a length of 10 mm and a density of 0.33 g/cm³ having a polyethylene terephthalate (PET) core and a polyethylene terephthalate (PET) sheath and a lower air permeability than the first sintered porous plastic plug. A suitable first porous plastic plug is Porex® XMF-0507 (available from Porex GmbH, Germany) and a suitable second porous plastic plug is Porex® XMF-0607 (available from Porex GmbH, Germany).

To form a nicotine source 10 µl of nicotine is sorbed by capillarity onto a sintered porous plastic plug with a length of 50 mm and a density of 0.33 g/cm³ having a polyethylene terephthalate (PET) core and a polyethylene (PE) sheath. A suitable porous plastic plug is Porex® XMF-0507 (available from Porex GmbH, Germany).

An aerosol-generating article according to the invention having the construction shown in FIG. 1(b) is assembled comprising the pyruvic acid source and the nicotine source. The second sintered porous plastic plug of the pyruvic acid source is positioned immediately downstream of and abutting the first sintered porous plastic plug of the pyruvic acid source and the nicotine source is positioned 10 mm downstream of the second sintered porous plastic plug of the pyruvic acid source.

EXAMPLE (c)

To form a pyruvic acid source 250 µl of pyruvic acid is sorbed by capillarity onto a first sintered porous plastic plug with a length of 10 mm and a density of 0.33 g/cm³ having a polyethylene terephthalate (PET) core and a polyethylene (PE) sheath and 100 µl of pyruvic acid is sorbed by capillarity onto a second sintered porous plastic plug with a length of 10 mm and a density of 0.33 g/cm³ having a polyethylene terephthalate (PET) core and a polyethylene terephthalate (PET) sheath and a lower air permeability than the first sintered porous plastic plug. A suitable first porous plastic plug is Porex® XMF-0507 (available from Porex GmbH, Germany) and a suitable second porous plastic plug is Porex® XMF-0607 (available from Porex GmbH, Germany).

To form a nicotine source 10 µl of nicotine is sorbed by capillarity onto a sintered porous plastic plug with a length of 50 mm and a density of 0.33 g/cm³ having a polyethylene terephthalate (PET) core and a polyethylene (PE) sheath. A suitable porous plastic plug is Porex® XMF-0507 (available from Porex GmbH, Germany).

An aerosol-generating article according to the invention having the construction shown in FIG. 1(b) is assembled comprising the pyruvic acid source and the nicotine source. The second sintered porous plastic plug of the pyruvic acid source is positioned 2 mm downstream of the first sintered porous plastic plug of the pyruvic acid source and the nicotine source is positioned 10 mm downstream of the second sintered porous plastic plug of the pyruvic acid source.

EXAMPLE (d)

To form a pyruvic acid source 250 µl of pyruvic acid is sorbed by capillarity onto a first sintered porous plastic plug with a length of 10 mm and a density of 0.33 g/cm³ having a polyethylene terephthalate (PET) core and a polyethylene (PE) sheath and 100 µl of pyruvic acid is sorbed by capillarity onto a second sintered porous plastic plug with a length of 10 mm and a density of 0.3 g/cm³ having a polyethylene terephthalate (PET) core, a polyethylene (PE) sheath and a viscose B fibre filling and a lower air permeability than the first sintered porous plastic plug. A suitable first porous plastic plug is Porex® XMF-0507 (available from Porex GmbH, Germany) and a suitable second sintered porous plastic plug is Porex® XMF-0130+B (available from Porex GmbH, Germany).

To form a nicotine source 10 µl of nicotine is sorbed by capillarity onto a sintered porous plastic plug with a length of 50 mm and a density of 0.33 g/cm³ having a polyethylene terephthalate (PET) core and a polyethylene (PE) sheath. A suitable porous plastic plug is Porex® XMF-0507 (available from Porex GmbH, Germany).

An aerosol-generating article according to the invention having the construction shown in FIG. 1(b) is assembled comprising the pyruvic acid source and the nicotine source. The second sintered porous plastic plug of the pyruvic acid source is positioned immediately downstream of and abutting the first sintered porous plastic plug of the pyruvic acid source and the nicotine source is positioned 10 mm downstream of the second sintered porous plastic plug of the pyruvic acid source.

EXAMPLE (e)

To form a pyruvic acid source 250 µl of pyruvic acid is sorbed by capillarity onto a first sintered porous plastic plug with a length of 10 mm and a density of 0.33 g/cm$^3$ having a polyethylene terephthalate (PET) core and a polyethylene (PE) sheath and 100 µl of pyruvic acid is sorbed by capillarity onto a second sintered porous plastic plug with a length of 10 mm and a density of 0.15 g/cm$^3$ having a polyethylene terephthalate (PET) core, a polyethylene (PE) sheath and a viscose B fibre filling and a lower air permeability than the first sintered porous plastic plug. A suitable first porous plastic plug is Porex® XMF-0507 (available from Porex GmbH, Germany) and a suitable second sintered porous plastic plug is Porex® XMF-0130+B (available from Porex GmbH, Germany).

To form a nicotine source 10 µl of nicotine is sorbed by capillarity onto a sintered porous plastic plug with a length of 50 mm and a density of 0.33 g/cm$^3$ having a polyethylene terephthalate (PET) core and a polyethylene (PE) sheath. A suitable porous plastic plug is Porex® XMF-0507 (available from Porex GmbH, Germany).

An aerosol-generating article according to the invention having the construction shown in FIG. 1(b) is assembled comprising the pyruvic acid source and the nicotine source. The second sintered porous plastic plug of the pyruvic acid source is positioned immediately downstream of and abutting the first sintered porous plastic plug of the pyruvic acid source and the nicotine source is positioned 10 mm downstream of the second sintered porous plastic plug of the pyruvic acid source.

EXAMPLE (f)

To form a pyruvic acid source 320 µl of pyruvic acid is sorbed by capillarity onto a first sintered porous plastic plug with a length of 10 mm and a density of 0.3 g/cm$^3$ having a polyethylene terephthalate (PET) core, a polyethylene (PE) sheath and a viscose B fibre filling sintered and 100 µl of pyruvic acid is sorbed by capillarity onto a second porous plastic plug with a length of 10 mm and a density of 0.33 g/cm$^3$ having a polyethylene terephthalate (PET) core and a polyethylene terephthalate (PET) sheath and a lower air permeability than the first sintered porous plastic plug. A suitable first porous plastic plug is Porex® XMF-130+B (available from Porex GmbH, Germany) and a suitable second sintered porous plastic plug is Porex® XMF-607 (available from Porex GmbH, Germany).

To form a nicotine source 10 µl of nicotine is sorbed by capillarity onto a sintered porous plastic plug with a length of 50 mm and a density of 0.33 g/cm$^3$ having a polyethylene terephthalate (PET) core and a polyethylene (PE) sheath. A suitable porous plastic plug is Porex® XMF-0507 (available from Porex GmbH, Germany).

An aerosol-generating article according to the invention having the construction shown in FIG. 1(b) is assembled comprising the pyruvic acid source and the nicotine source. The second sintered porous plastic plug of the pyruvic acid source is positioned immediately downstream of and abutting the first sintered porous plastic plug of the pyruvic acid source and the nicotine source is positioned 10 mm downstream of the second sintered porous plastic plug of the pyruvic acid source.

EXAMPLE (g)

To form a pyruvic acid source 320 µl of pyruvic acid is sorbed by capillarity onto a first sintered porous plastic plug with a length of 10 mm and a density of 0.15 g/cm$^3$ having a polyethylene terephthalate (PET) core, a polyethylene (PE) sheath and a viscose B fibre filling sintered and 100 µl of pyruvic acid is sorbed by capillarity onto a second porous plastic plug with a length of 10 mm and a density of 0.33 g/cm$^3$ having a polyethylene terephthalate (PET) core and a polyethylene terephthalate (PET) sheath and a lower air permeability than the first sintered porous plastic plug. A suitable first porous plastic plug is Porex® XMF-130+B (available from Porex GmbH, Germany) and a suitable second sintered porous plastic plug is Porex® XMF-607 (available from Porex GmbH, Germany).

To form a nicotine source 10 µl of nicotine is sorbed by capillarity onto a sintered porous plastic plug with a length of 50 mm and a density of 0.33 g/cm$^3$ having a polyethylene terephthalate (PET) core and a polyethylene (PE) sheath. A suitable porous plastic plug is Porex® XMF-0507 (available from Porex GmbH, Germany).

An aerosol-generating article according to the invention having the construction shown in FIG. 1(b) is assembled comprising the pyruvic acid source and the nicotine source. The second sintered porous plastic plug of the pyruvic acid source is positioned immediately downstream of and abutting the first sintered porous plastic plug of the pyruvic acid source and the nicotine source is positioned 10 mm downstream of the second sintered porous plastic plug of the pyruvic acid source.

The nicotine yield per group of five puffs of the aerosol-generating articles of comparative example (a) and examples (b) to (g) is measured under a Health Canada smoking regime over 30 puffs with a puff volume of 55 ml, puff duration of 2 seconds and a puff interval of 30 seconds. Each group of five puffs is collected on a Cambridge filter pad and then extracted with a liquid solvent. The resulting liquid is analysed by gas chromatography to determine the nicotine delivery. The results are shown in FIGS. 2, 3 and 4.

Figure 2:
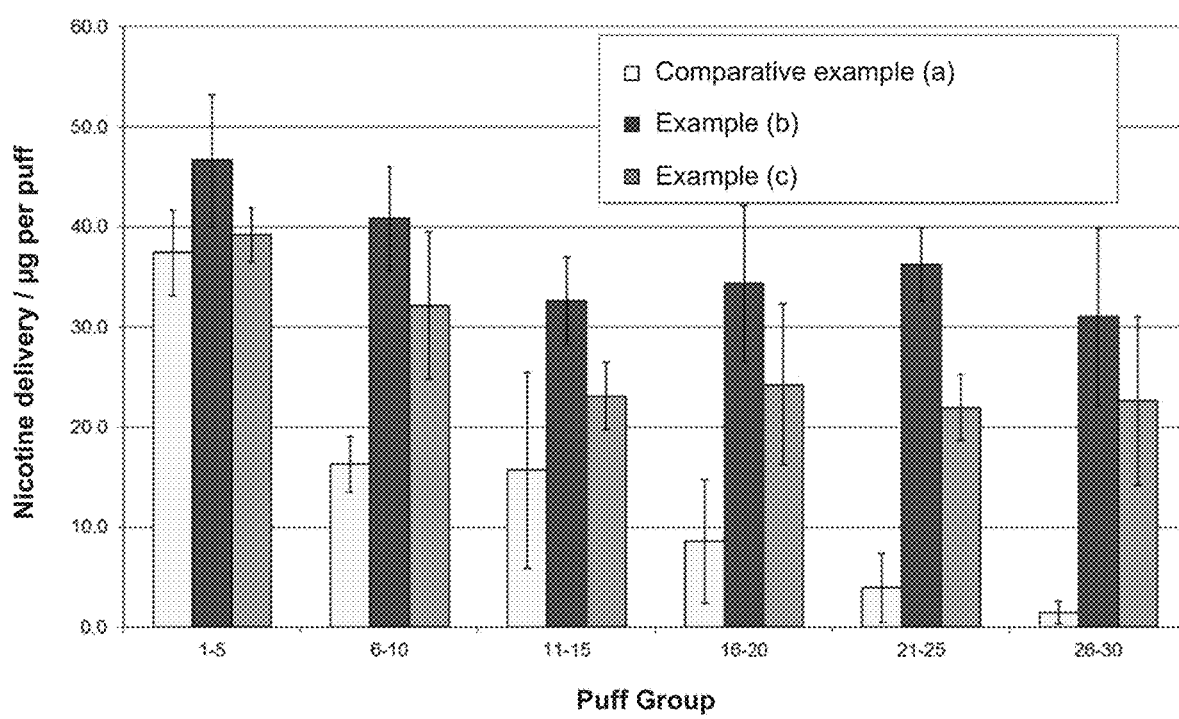
FIG. 2 shows the nicotine delivery per puff as a function of puff number for aerosol-generating articles according to: comparative example (a); example (b); and example (c) upon heating measured under a Health Canada smoking regime.

As shown in FIG. 2, the nicotine delivery of puffs 6-10, 11-15, 16-20, 21-25 and 26-30 of the aerosol-generating articles according to the invention of examples (b) and (c) is greater than that of the corresponding puffs of the prior art aerosol-generating article of comparative example (a). As a result, the inclusion in the aerosol-generating articles according to the invention of examples (b) and (c) of a pyruvic acid source comprising a first porous sorption element and a second porous sorption element downstream of the first sorption element, wherein the rate of release of the pyruvic acid from the first sorption element is greater than the rate of release of the pyruvic acid from the second sorption element, advantageously results in more consistent and sustained delivery of nicotine compared to the prior art aerosol-generating article of comparative example (a).

As shown in FIGS. 3 and 4, altering the properties of the first sorption element and the second sorption element and hence the difference in the rate of release of the pyruvic acid from the first sorption element and the second sorption element advantageously allows the nicotine delivery of the aerosol-generating articles according to the invention in examples (b) to (g) to be controlled.

The invention has been exemplified above by reference to aerosol-generating articles comprising delivery enhancing compound sources comprising porous plastic plugs having pyruvic acid adsorbed thereon and medicament sources comprising porous plastic plugs having nicotine adsorbed thereon. However, it will be appreciated that aerosol-generating articles and aerosol-generating systems according to the invention may comprise other sorption elements, other delivery enhancing compounds and other medicaments.

The invention claimed is:

1. An aerosol-generating system, comprising:
   a medicament source; and
   a volatile delivery enhancing compound source, comprising:
      a first sorption element;
      a second sorption element immediately downstream of and in contact with the first sorption element; and
      a volatile delivery enhancing compound sorbed on the first sorption element and the second sorption element,
   wherein a rate of release of the volatile delivery enhancing compound from the first sorption element is greater than a rate of release of the volatile delivery enhancing compound from the second sorption element.

2. The aerosol-generating system according to claim 1, wherein an air permeability of the first sorption element is greater than an air permeability of the second sorption element.

3. The aerosol-generating system according to claim 1, wherein a porosity of the first sorption element is greater than a porosity of the second sorption element.

4. The aerosol-generating system according to claim 1, wherein a polarity of the second sorption element is greater than a polarity of the first sorption element.

5. The aerosol-generating system according to claim 1, wherein the medicament source comprises:
   a third sorption element; and
   a medicament sorbed on the third sorption element.

6. The aerosol-generating system according to claim 5, wherein the medicament comprises nicotine.

7. The aerosol-generating system according to claim 1, wherein the volatile delivery enhancing compound comprises an acid.

8. The aerosol-generating system according to claim 7, wherein the acid is selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid, and combinations thereof.

9. The aerosol-generating system according to claim 7, wherein the acid is pyruvic acid.

10. The aerosol-generating system according to claim 1, wherein an amount of the volatile delivery enhancing compound sorbed on the first sorption element is greater than an amount of the volatile delivery enhancing compound sorbed on the second sorption element.

11. The aerosol-generating system according to claim 1, wherein the first sorption element is of the same dimensions as the second sorption element.

12. The aerosol-generating system according to claim 1, further comprising:
    an aerosol-generating article, comprising the medicament source and the volatile delivery enhancing compound source.

13. The aerosol-generating system according to claim 12, wherein the aerosol-generating article further comprises:
    a housing, comprising:
       an air inlet;
       a first compartment in communication with the air inlet, the first compartment comprising a first one of the medicament source and the volatile delivery enhancing compound source;
       a second compartment in communication with the first compartment, the second compartment comprising a second one of the medicament source and the volatile delivery enhancing compound source; and
       an air outlet,
    wherein the air inlet and the air outlet are in communication with each other and are configured to allow air to pass into the housing through the air inlet, through the housing, and out of the housing through the air outlet.

14. The aerosol-generating system according to claim 13, wherein one or both of the first compartment and the second compartment of the aerosol-generating article is sealed by one or more frangible seals.

15. The aerosol-generating system according to claim 13, wherein the first compartment comprises the volatile delivery enhancing compound source and the second compartment comprises the medicament source.

16. The aerosol-generating system according to claim 12, wherein the aerosol-generating article further comprises:
    a housing, comprising:
       an air inlet;
       a first compartment in communication with the air inlet, the first compartment comprising a first one of the medicament source and the volatile delivery enhancing compound source;
       a second compartment in communication with the air inlet, the second compartment comprising a second one of the medicament source and the volatile delivery enhancing compound source; and
       an air outlet,
    wherein the air inlet and the air outlet are in communication with each other and are configured to allow air to pass into the housing through the air inlet, through the housing, and out of the housing through the air outlet.

17. The aerosol-generating system according to claim 1, wherein the rate of release of the volatile delivery enhancing compound from the first sorption element is at least three times the rate of release of the volatile delivery enhancing compound from the second sorption element.

18. The aerosol-generating system according to claim 1, wherein the rate of release of the volatile delivery enhancing compound from the first sorption element is between about three times and about ten times the rate of release of the delivery enhancing compound from the second sorption element.

* * * * *